United States Patent [19]

Pividal et al.

[11] Patent Number: 5,693,191
[45] Date of Patent: Dec. 2, 1997

[54] PROCESS FOR RECOVERY OF ANHYDROUS HYDROGEN CHLORIDE FROM MIXTURES WITH NON-CONDENSABLE GASES

[75] Inventors: Katherine A. Pividal, Baton Rouge, La.; Tom C. Tsai, Houston, Tex.

[73] Assignee: The Dow Chemical Company, Midland, Mich.

[21] Appl. No.: 344,186

[22] Filed: Nov. 23, 1994

[51] Int. Cl.$^6$ ............................................. B01D 3/00
[52] U.S. Cl. ........................... 203/12; 203/29; 203/87; 203/98; 585/638; 585/641; 585/642; 588/206; 208/87; 208/89; 208/92; 208/100
[58] Field of Search .................... 203/12, 21, 22, 203/29, 87, 98; 202/163, 176, 180; 208/85, 87, 88, 89, 92, 94, 100, 104, 105, 184, 187; 95/39, 156; 585/638, 641, 642; 588/206

[56] References Cited

U.S. PATENT DOCUMENTS

| | | | |
|---|---|---|---|
| 3,892,818 | 7/1975 | Scharfe et al. | 260/676 R |
| 3,968,178 | 7/1976 | Obrecht et al. | 423/488 X |
| 4,558,167 | 12/1985 | Riegel et al. | 570/238 |
| 4,634,784 | 1/1987 | Nagato et al. | 549/521 |
| 4,818,368 | 4/1989 | Kalnes et al. | 208/50 |
| 4,830,846 | 5/1989 | Jackson et al. | 423/488 |
| 4,840,721 | 6/1989 | Kalnes et al. | 208/57 |
| 4,882,037 | 11/1989 | Kalnes et al. | 208/85 |
| 4,895,995 | 1/1990 | James, Jr. et al. | 585/310 |
| 4,899,001 | 2/1990 | Kalnes et al. | 585/310 |
| 4,923,590 | 5/1990 | Kalnes et al. | 208/85 |
| 4,927,621 | 5/1990 | Repman et al. | 428/488 |
| 5,174,865 | 12/1992 | Stulz et al. | 203/12 |
| 5,314,614 | 5/1994 | Moser et al. | 208/262.1 |
| 5,316,663 | 5/1994 | James, Jr. | 208/262.1 |
| 5,453,557 | 9/1995 | Harley et al. | 585/641 |

FOREIGN PATENT DOCUMENTS

531836A1  8/1992  European Pat. Off. .

OTHER PUBLICATIONS

Removal of organic compounds from gaseous hydrogen chloride by the absorption method.
Journal from Chemia Stosowana214–218 1980 J. Myszkowski, W. Pazdzioch, J. Zalinska–Gawronska, M. Antoszczyszyn, W. Goc and M. Szymroszczyk.

Primary Examiner—Christopher Kim

[57] ABSTRACT

A process is provided for the recovery of hydrogen chloride in anhydrous form from a dry (containing less than about 500 parts per million by weight of water) mixture of hydrogen chloride with one or more non-condensable gases and which may also contain components heavier than hydrogen chloride, which process comprises distilling the mixture to produce an overheads stream containing the non-condensable gases and about 95 percent or more by weight of the hydrogen chloride in the mixture and a bottoms stream containing about 95 percent or greater by weight of all components heavier than hydrogen chloride, and compressing and refrigerating the overheads stream whereby a selected proportion of the hydrogen chloride in the overheads stream is produced in a liquid anhydrous form containing less than about 50 parts per million by weight of water.

25 Claims, 1 Drawing Sheet

PROCESS FOR RECOVERY OF ANHYDROUS HYDROGEN CHLORIDE FROM MIXTURES WITH NON-CONDENSABLE GASES

BACKGROUND OF THE INVENTION

The present invention relates to processes for separating out and recovering hydrogen chloride from mixtures including non-condensable gases such as hydrogen. More particularly, the present invention relates to processes which are able to recover hydrogen chloride from such mixtures in a desirable anhydrous form.

A number of processes are described in the art for converting a chlorinated hydrocarbon feedstock to a less-chlorinated hydrocarbon or hydrocarbons and hydrogen chloride, by reaction of the chlorinated hydrocarbon feedstock with hydrogen over a selected catalyst.

Exemplary of these processes are those described in EP 015665 (converting 1,1,2-trichloroethane to ethylene or vinyl chloride), GB 1 400 529 (converting "hydrocarbon chlorides" to "chlorine-free hydrocarbons"), DE 235 630 A1 (converting 1,2-dichloropropane to propylene), U.S. Pat. No. 4,818,368, 4,882,037 and 4,923,590 (the hydrogenation of halogenated hydrocarbons), CA 1 119 203 (converting perchloroethylene to trichloroethylene), DE 3 804 265 A1 (same) and U.S. Pat. No. 5,091,603 (same).

Commonly-assigned WO 94/07828 is also relevant, in describing a process for converting 1,2-dichloropropane (a significant co-product of the chlorohydrin process for making propylene oxide from propylene) to propylene and hydrogen chloride.

Each of these processes produces a product stream from a reactor section thereof which contains the desired less-chlorinated hydrocarbon product(s), hydrogen chloride and unreacted hydrogen in some amount, generally along with some unconverted chlorinated hydrocarbon feedstock and some less-chlorinated byproducts.

Those processes which have been known in the art prior to the making of the present invention for separating the hydrogen chloride and heavier materials from the non-condensable unreacted hydrogen and other non-condensable gases which may conceivably be present in smaller amounts in the product streams from these processes, e.g., methane, carbon monoxide and nitrogen, are less than completely satisfactory.

For example, U.S. Pat. No. 5,314,614 and 5,316,663 describe related processes wherein the effluent from a hydrogenation reaction zone is introduced into a "vapor-liquid separator" at essentially the same pressure as employed in the hydrogenation reaction zone (i.e., atmospheric to 2000 psig, and especially 100 psig to 1800 psig) and at temperatures ranging from −57 degrees Celsius to 16 degrees Celsius in the case of the the '614 patent (as compared to reaction temperatures of from 10 degrees Celsius to 450 degrees Celsius), or from −57 degrees Celsius to 4.4 degrees Celsius in the '663 patent (reaction temperatures of 50 degrees Celsius to 454 degrees Celsius).

In the '614 patent, a hydrogen-rich gaseous recycle stream is produced for recycle to the reaction zone which also contains hydrogen halide, the amount of hydrogen halide being controlled by a selection of pressure and temperature in the vapor-liquid separator to minimize the decomposition or undesirable polymerization of thermally unstable compounds in the feedstock to the hydrogenation reaction zone. In the '663 patent, the feedstock is not expressly described as necessarily containing the thermally unstable compounds of the '614 patent, and the vapor-liquid separator is said simply to produce a hydrogen-rich gaseous recycle stream.

In both patents, the liquid hydrocarbonaceous stream from the vapor-liquid separator is then described as being separated, for example by stripping, flashing or fractionating, to produce an anhydrous hydrogen halide stream and a liquid hydrocarbonaceous stream, the liquid hydrocarbonaceous stream then being separated to produce a hydrogenated hydrocarbonaceous product stream containing a reduced level of halogen and a stream primarily comprised of halogenated organic compounds for possible recycle to the hydrogenation reaction zone.

The only example provided to demonstrate the separation capabilities of the described processes under the prescribed conditions of pressure and temperature in the vapor-liquid separator is found in the Example in the '663 patent, wherein the effluent from a hydrogenation reaction zone operating at 80 degrees Celsius and a pressure of 5171 kPa gauge (or 750 psig) was cooled to a temperature of about −15 degrees Celsius and introduced into the vapor-liquid separator. The hydrogen-rich gaseous recycle stream from the separator was comprised of about 2000 mols/hr of hydrogen, 850 mols/hr of hydrogen chloride and 70 mols/hr of chlorinated hydrocarbons, whereas the liquid hydrocarbonaceous stream (from which anhydrous hydrogen chloride was subsequently recovered as a product stream) contained a total of 140 mols/hr of non-chlorinated hydrocarbon (in this case propane, at 50 mols/hr), hydrogen chloride (60 mols/hr) and chlorinated hydrocarbons (25 mols/hr). Consequently, more than 93 percent of the hydrogen chloride in the effluent was not recovered in the vapor-liquid separator as anhydrous hydrogen chloride.

Other conventional approaches to separating hydrogen and other non-condensable gases from hydrogen chloride and heavier materials in the effluent from a catalytic process for the conversion of a chlorinated hydrocarbon feedstock to a desired less-chlorinated hydrocarbon and hydrogen chloride have included absorption in water or in an HCl-lean scrubbing solution, or neutralization of the hydrogen chloride followed by a vapor-liquid separation, see, for example, U.S. Pat. No. 4,899,001 and 4,929,781. These approaches are limited at best to the production of concentrated hydrochloric acid, and consequently may implicate certain, expensive materials of construction as well as the other particular concerns and considerations associated with the manufacture of concentrated hydrochloric acid.

SUMMARY OF THE PRESENT INVENTION

In the very broadest sense, the present invention concerns a process for the recovery of hydrogen chloride in anhydrous form from a dry (containing less than about 500 parts per million by weight of water) mixture of hydrogen chloride, one or more non-condensable gases and such heavier components as may additionally be present in the mixture, which process comprises distilling the mixture to produce an overheads stream containing the non-condensable gases and about 95 percent or more by weight of the hydrogen chloride in the mixture and a bottoms stream containing about 95 percent or greater by weight of all components heavier than hydrogen chloride, and compressing and refrigerating the overheads stream using available refrigeration, whereby a selected proportion of the hydrogen chloride in the overheads stream is produced in a liquid anhydrous form containing less than about 50 parts per million by weight of water.

In the context of a preferred application, it will be seen that a process is enabled wherein hydrogen chloride in a product stream from reacting a chlorinated hydrocarbon feedstock (dry, i.e., containing less than about 500 parts per million by weight of water and, in some contexts, water precursors such as oxygenated compounds which when subjected to process conditions in the presence of certain catalysts, are converted in part to water) and hydrogen over a selected catalyst to produce a less-chlorinated hydrocarbon or less-chlorinated hydrocarbons and said hydrogen chloride, may be separated from non-condensable gases such as unreacted hydrogen in such product stream, and economically recovered in a desired amount in anhydrous form without the need for excessive refrigeration of the product stream as a whole. The term "anhydrous", when used to denote the hydrogen chloride-containing product stream thus separated out and recovered, is to be understood henceforth as referring to a product stream containing less than about 50 parts per million by weight of water.

The process of the present invention when applied in this preferred context fundamentally involves distilling the product stream from the reactor section at pressures equal to or greater than the reaction pressure employed in the preceding reactive process, but preferably at substantially the same pressure, to produce a bottoms stream comprising the less-chlorinated hydrocarbon or hydrocarbons and an overheads stream comprising substantially all of the hydrogen chloride in the product stream, together with unreacted hydrogen and any other non-condensable gases which may be present in the product stream.

The bottoms stream is processed by conventional means to recover the desired less-chlorinated hydrocarbon or hydrocarbons, for example, by distilling to separate the desired less-chlorinated hydrocarbon or hydrocarbons and any unreacted chlorinated hydrocarbon feedstock, which unreacted feedstock may then be recycled to the reactive process for being converted to the desired products. The desired less-chlorinated hydrocarbon or hydrocarbons may be disposed of, sold, incinerated or used in another process, as will be seen.

The overheads stream from the distillation step is compressed and refrigerated with available refrigeration to produce a desired proportion of the hydrogen chloride in the overheads stream as liquid anhydrous hydrogen chloride, such proportion being determined by selecting a compressor discharge pressure for the compression of the overheads stream.

Hydrogen chloride not condensed from the overheads stream may in a further step be absorbed in water or an HCl-lean scrubbing solution or neutralized with a base, while the hydrogen chloride condensed from such overheads stream in liquid anhydrous form may preferably be recovered in greater purity by passing some or all of the anhydrous hydrogen chloride stream through a degassing or flashing apparatus. The unreacted hydrogen and other non-condensables remaining after such absorption and/or degassing may be recycled to the preceding reactive process.

DETAILED DESCRIPTION OF THE PREFERRED EMBODIMENT

Figure 1:
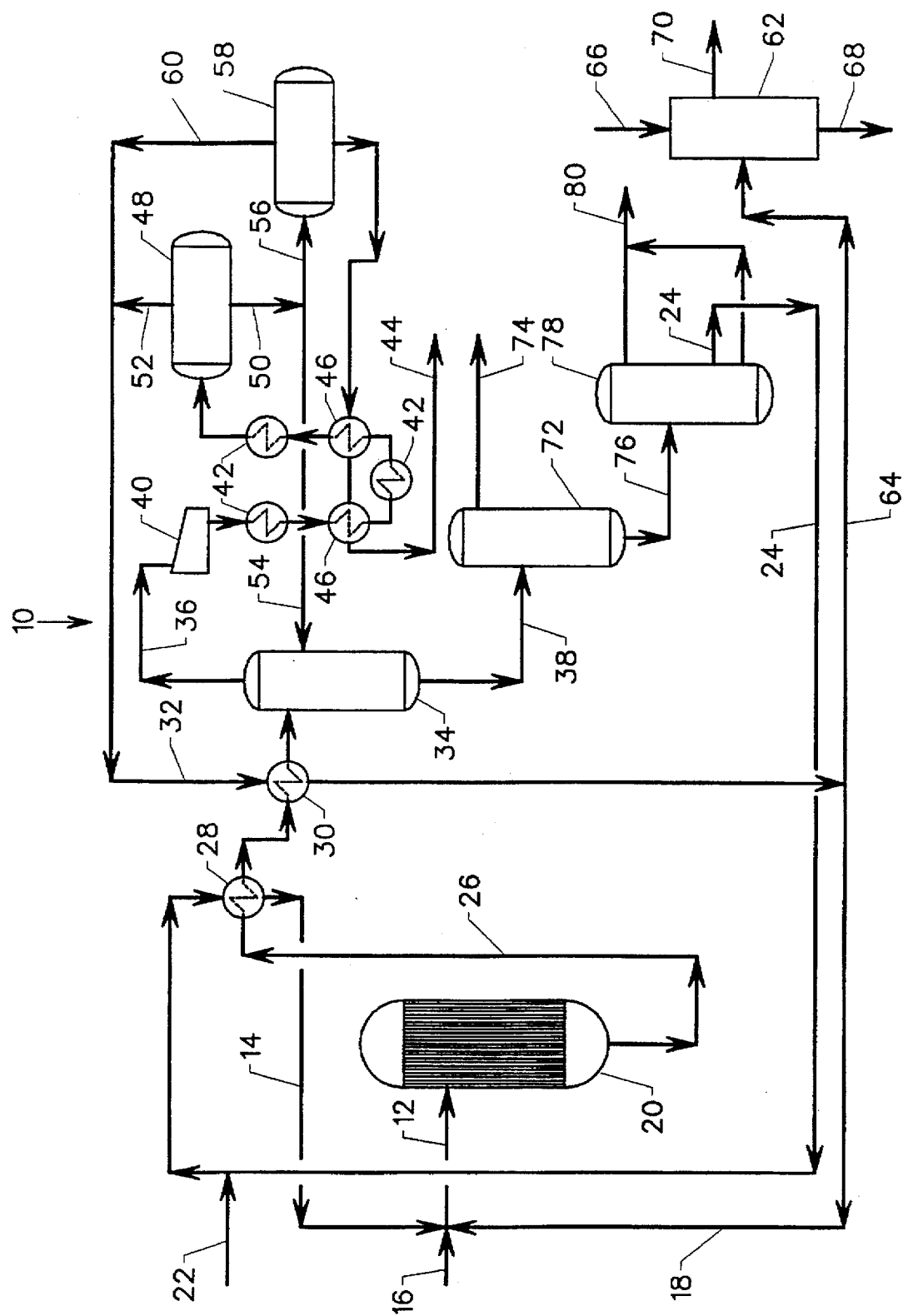
FIG. 1 illustrates a preferred process of the present invention for separating out and recovering hydrogen chloride in anhydrous form from a product stream containing hydrogen chloride and non-condensable gases such as hydrogen, such product stream being produced in a reactive process for converting a chlorinated hydrocarbon feedstock to a less-chlorinated hydrocarbon or hydrocarbons and hydrogen chloride.

A preferred process 10 is illustrated in FIG. 1 for converting a chlorinated hydrocarbon feedstock to a less-chlorinated hydrocarbon or hydrocarbons and hydrogen chloride, and thereafter recovering the desired less-chlorinated hydrocarbon and anhydrous hydrogen chloride. For convenience and ease of understanding, a number of conventional details and elements of the illustrated process have been omitted, and for example, a single reactor is illustrated as being employed when more than one reactor may be employed in series or in parallel according to conventional practice in the processing of certain chlorinated hydrocarbon-containing feedstocks, see, for example, U.S. Pat. No. 4,895,995 to James Jr. et al. and the aforementioned U.S. Pat. No. 4,899,001 to Kalnes et al.

Those skilled in the art will additionally readily appreciate that numerous arrangements and variations of apparatus are conventionally possible for generating a dry product stream containing hydrogen chloride and one or more non-condensable gases from a given chlorinated hydrocarbon-containing feedstock, from which anhydrous hydrogen chloride may be recovered in keeping with the process of the present invention. Illustrative of the arrangements and variations of apparatus which may conceivably be combined through the exercise of routine skill with the separation process of the present invention are those described in a number of U.S. Patents assigned to UOP, Des Plaines, Ill., U.S.A., e.g., U.S. Pat. Nos. 4,747,937, 4,818,368, 4,840, 721, 4,882,037, 4,895,995, 4,923,590, 4,927,520 and 5,013, 424.

Referring now to the preferred process 10 illustrated in FIG. 1, however, a reactor feed 12 which is comprised of a combined chlorinated hydrocarbon feedstock stream 14, a makeup hydrogen stream 16 and a combined hydrogen/hydrogen chloride recycle stream 18, is fed to a reactor 20. The combined chlorinated hydrocarbon feedstock stream 14 in turn is comprised of a fresh chlorinated hydrocarbon feedstock stream 22 and a recycle chlorinated hydrocarbon feedstock stream 24 which contains unconverted feedstock recovered in downstream processing.

Suitable chlorinated hydrocarbon feedstocks and the associated reactive processes can be any of those mentioned previously, but are generally and preferably directed to the conversion of one or more significant co-products or waste products from another commercial process. Non-limiting examples would be the conversion of waste or less desirable co-product chlorinated $C_3$ hydrocarbons from a chlorohydrin process of making propylene oxide or from allyl chloride/epichlorohydrin production, and waste or less desirable co-product chlorinated $C_2$ hydrocarbons from the production of vinyl chloride via ethylene dichloride.

It will be understood, however, that conceivably any chlorinated hydrocarbon feedstock and associated reactive process may be employed which can produce a dry (i.e., containing less than about 500 parts per million by weight of water or water precursors) product stream 26 containing a desired less-chlorinated hydrocarbon or hydrocarbons and hydrogen chloride, along with some unreacted hydrogen and perhaps some additional non-condensable gases such as methane, carbon monoxide and nitrogen.

A preferred application of the invention is for the conversion of 1,2-dichloropropane (hereafter, PDC) to propylene (as the desired less-chlorinated hydrocarbon) and hydrogen chloride by reaction with hydrogen in the vapor phase over a catalyst, and most particularly over a carbonsupported, platinum/copper catalyst according to a process described in detail in the aforementioned WO 94/07828 published patent application under the Patent Cooperation Treaty (such published patent application being incorporated herein by reference).

In the context of such a PDC to propylene process, a dry gaseous product stream 26 containing principally hydrogen, hydrogen chloride and propylene is produced in reactor 20 and preferably cross-exchanged with the combined PDC stream 14 in exchanger 28, before the stream 14 is combined in the reactor feed 12. The product stream 26 is cross-exchanged also in an exchanger 30 with hydrogen/hydrogen chloride vapor stream 32 (the origin of which will be described subsequently, and from which combined hydrogen/hydrogen chloride recycle stream 18 is derived). The heat exchange in exchangers 28 and 30 at least partially condenses the product stream 26, whereupon the product stream 26 is fed to a distillation apparatus at a temperature on the order of, for example, about 30 to about 35 degrees Celsius, and distilled therein at a pressure which is substantially the same as the reaction pressure employed in the reactor 20. A compressor may be employed for compressing the product stream 26 to a pressure which is greater than that in the reactor 20, and which may approach the pressure required given available refrigeration to achieve a selected proportion of liquid anhydrous hydrogen chloride from an overheads stream 36 from the distillation apparatus 34. Preferably, however, the product stream 26 is distilled at a pressure which is substantially equal to that found in the reactor 20.

Overheads stream 36 contains substantially all (e.g., about 95 percent or more by weight and especially about 99.99 percent or more by weight) of the hydrogen chloride in the product stream 26, together with the unreacted hydrogen in the product stream 26 and any smaller amounts of other non-condensable gases present in the product stream 26. A bottoms stream 38 is also produced containing substantially all (e.g., about 95 percent or more by weight, and especially about 99.5 percent or more by weight) of the propylene from product stream 26, as well as unreacted PDC and any partially hydrodechlorinated chlorinated hydrocarbons, such as 2-chloropropane.

The overheads stream 36 is compressed in a compressor apparatus 40 and preferably both air-cooled and refrigerated with an available refrigeration source (e.g., intermediated stage propylene refrigeration) in exchangers 42, while also preferably being cross-exchanged with a subsequently-produced liquid anhydrous hydrogen chloride product stream 44 in one or more exchangers 46.

Thereafter the overheads stream 36 is passed to a reflux drum 48 to produce a liquid anhydrous hydrogen chloride source stream 50 and a vapor stream 52 containing hydrogen, hydrogen chloride and any other non-condensable inerts which may have been present in the overheads stream 36, with the distribution between the hydrogen chloride recovered in the liquid anhydrous hydrogen chloride source stream 50 and hydrogen chloride remaining in the vapor stream 52 being controlled by selection of the compressor discharge pressure (a higher compressor discharge pressure resulting at the same refrigeration load in a greater proportion of the hydrogen chloride being recovered in liquid anhydrous hydrogen chloride source stream 50).

A significant degree of flexibility is consequently entailed in the present invention for tailoring the amounts of hydrogen chloride produced in anhydrous form based on the demand for such as compared to the costs of compression and refrigeration, based on the need for concentrated aqueous hydrochloric acid in other applications, and/or based on the benefits purportedly obtainable from recycling a certain amount of hydrogen chloride to the reactor 20 for processing certain chlorinated hydrocarbon feedstocks in terms of more stable catalyst activity, reduced deactivation and longer catalyst lifetimes, see, for example, U.S. Pat. No. 5,314,614 to Moser et al., all without modifying the operating conditions of the distillation apparatus 34 and by simply altering the compressor discharge pressure and amount of refrigeration performed on overheads stream 36.

Returning now to considering FIG. 1, a reflux portion of the liquid hydrogen chloride source stream 50 is refluxed back to the distillation apparatus 34 in reflux stream 54. As the stream 50 from the reflux drum 48 is saturated with hydrogen and any other non-condensables present in the overheads stream 36, that portion of the stream 50 not refluxed to the distillation apparatus 34 is preferably then conveyed in a stream 56 to be degassed or flashed in a vessel 58 at a lower pressure to remove residual hydrogen or other non-condensable materials. Residual hydrogen and other non-condensable materials which may be removed in this fashion are recycled to the reactor 20 in a vapor stream 60 along with vapor stream 52 from reflux drum 48. As can be seen in FIG. 1, vapor streams 52 and 60 from reflux drum 48 and vessel 58, respectively, combine to form hydrogen/hydrogen chloride vapor stream 32. A portion or all of hydrogen/hydrogen chloride vapor stream 32 is recycled to the reactor 20 as combined hydrogen/hydrogen chloride recycle stream 18, with any remaining portion of the hydrogen/hydrogen chloride vapor stream 32 being routed to a scrubber 62 in a stream 64 to produce concentrated aqueous hydrochloric acid (as described below).

A purified liquid anhydrous hydrogen chloride product stream 44 is thereby produced which again is preferably cross-exchanged with the compressed overheads stream 36 in one or more exchangers 46, to reduce refrigeration requirements for condensing hydrogen chloride out of overheads stream 36 and recovering the same in reflux drum 48 through vaporization or partial vaporization of the liquid anhydrous hydrogen chloride product stream 44.

Hydrogen chloride not condensed from the overheads stream 36 and remaining in the vapor streams 52 and 60 from the reflux drum 48 and vessel 58 is preferably recycled in combined hydrogen/hydrogen chloride recycle stream 18 to the reactor 20, or as just noted is passed in a stream 64 into a scrubber 62 for being absorbed in a flow 66 of water or an HCl-lean scrubbing solution, thus producing a concentrated hydrochloric acid product stream 68. Hydrogen and other non-condensables in the streams 52 and 60 are conveyed in a stream 70 to be burned. Alternatively, the hydrogen chloride is conventionally neutralized in vessel 62 with a flow 66 of a base, conveniently, an aqueous solution of potassium hydroxide, calcium hydroxide or sodium hydroxide, to produce a brine solution 68. Preferably however the hydrogen chloride is recovered in the form of a concentrated aqueous hydrochloric acid stream 68, with the proportion of hydrogen chloride recovered in anhydrous form versus concentrated aqueous form being determined by the selection of a compressor discharge pressure for compressor 40.

The bottoms stream 38 from the distillation apparatus 34, containing substantially all of the propylene from product stream 26, as well as unreacted PDC and any partially hydrodechlorinated chlorinated hydrocarbons such as 2-chloropropane, is preferably further processed in a conventional distillation apparatus 72 to recover an overhead propylene stream 74 in an acceptable purity for subsequent sale or use, for example in being recycled to a source chlorohydrin process for making propylene oxide or to an allyl chloride process. The unreacted PDC and other remaining chlorinated hydrocarbons are conveyed in a bottoms stream 76 to another conventional distillation apparatus 78, wherein the PDC recycle stream 24 originates and is recycled to be combined with fresh PDC feed stream 22 to form the combined PDC stream 14. Partially hydrodechlorinated chlorinated hydrocarbons and any heavier, tarry materials which may be present starting in the fresh PDC feed stream 22 can be removed from the apparatus 78 via a stream 80 and incinerated or otherwise disposed of, it being understood that the precise nature of these remaining materials to be incinerated will be dependent at least on the source of the chlorinated hydrocarbon feedstock and the process and process conditions used in and prevailing in the reactor 20.

As has been mentioned previously, the process arrangement of FIG. 1 is offered as illustrative only of the process of the present invention in a preferred environment or user other uses being contemplated as well as other arrangements being possible and perhaps preferable in the preferred use when given a particular chlorinated hydrocarbon feedstock.

This having been said, the present invention is still more particularly illustrated by the following example:

ILLUSTRATIVE EXAMPLE

For this example, a process simulation was performed using software developed by Aspen Technology Inc., Cambridge Mass., on the distillation of the product stream from a hydrodechlorination of 1,2-dichloropropane, the product stream in question being comprised of hydrogen and other noncondensable inerts such as methane (0.2100 mole fraction of non-condensables), hydrogen chloride (0.3850 mole fraction), propylene (0.1820 mole fraction), isopropylchloride (0.0200 mole fraction) and 1,2-dichloropropane (0.2030 mole fraction).

Vapor-liquid equilibria data were taken in a conventional manner for use in this simulation, and necessary overheads and bottoms temperatures and pressures determined for the recovery of greater than 99.99 percent of the hydrogen chloride in the overheads and 99.5 percent of the propylene in the bottoms, assuming a feed temperature of 35 degrees Celsius and a feed pressure of 6 bars absolute.

In the absence of compression, all of the hydrogen chloride is recovered in combination with the noncondensable, inert fraction in the vapor phase, and the desired separation between hydrogen chloride and propylene is achieved with an overheads temperature (at 6 bars absolute) of −55 degrees Celsius, versus a 30 deg. C. bottoms temperature.

With the addition of a compressor, the desired separation may be achieved at an overheads temperature of −40 degrees Celsius and an overheads pressure of 13 bars absolute, all of the hydrogen chloride again however being combined with the noncondensable fraction. Additional compression to 22 bars (at the same temperature of −40 degrees Celsius) resulted in 38 percent of the hydrogen chloride remaining with hydrogen in the vapor phase, with 62 percent being found in liquid form. Degassing at a reduced pressure of 8 bars and at −45 degrees Celsius provided a purified liquid anhydrous hydrogen chloride stream containing 60 percent by weight of the hydrogen chloride originally in the product stream, whereas 2 percent was carried over in the vapor stream from the degasset.

What is claimed is:

1. A process for recovering hydrogen chloride in anhydrous form from a dry mixture of hydrogen chloride and one or more non-condensable gases, and components heavier than hydrogen chloride, which process comprises the steps of:

distilling the mixture to produce an overheads stream containing the one or more non-condensable gases and about 95 percent or more by weight of the hydrogen chloride in the mixture and a bottoms stream containing about 95 percent or greater by weight of the sum in the mixture of all components heavier than hydrogen chloride; and compressing and refrigerating the overheads stream whereby a selected proportion of the hydrogen chloride in the overheads stream is produced in a liquid anhydrous form containing less than about 50 parts per million by weight of water.

2. A process for recovering hydrogen chloride in anhydrous form from a product stream from a catalytic process wherein a chlorinated hydrocarbon feedstock containing less than about 500 parts per million by weight of water or water precursors is reacted with hydrogen to produce a less-chlorinated hydrocarbon or less-chlorinated hydrocarbons and hydrogen chloride, comprising the steps of:

distilling the product stream from such catalytic process at a pressure equal to or greater than employed in reacting the chlorinated hydrocarbon and hydrogen in said catalytic process, to produce a bottoms stream comprising about 95 percent by weight or more of the less-chlorinated hydrocarbon or hydrocarbons in the product stream and an overheads stream comprising about 95 percent by weight or greater of the hydrogen chloride in the product stream, together with unreacted hydrogen and any other non-condensable gases from said product stream; and compressing and refrigerating the overheads stream to produce a desired proportion of the hydrogen chloride in the overheads stream in a liquid anhydrous form, and a vapor stream containing substantially all of the unreacted hydrogen and other non-condensable gases if any from said overheads stream.

3. A process as defined in claim 2, further comprising distilling the bottoms stream to recover the less-chlorinated hydrocarbon or hydrocarbons in the product stream and to enable recycling of unreacted chlorinated hydrocarbon feedstock to the catalytic process.

4. A process as defined in claim 2, wherein the bottoms stream resulting from the distillation of the product stream contains about 99.5 percent by weight or more of the less-chlorinated hydrocarbon or hydrocarbons in said product stream.

5. A process as defined in claim 2, wherein the distillation of the product stream is performed at a pressure which is substantially the same as employed in the process of reacting the chlorinated hydrocarbon feedstock with hydrogen to produce said product stream.

6. A process as defined in claim 2, wherein the overheads stream from the distillation of said product stream contains about 99.99 percent by weight or greater of the hydrogen chloride in the product stream.

7. A process as defined in claim 2, wherein a portion of the liquid anhydrous hydrogen chloride-containing stream from the compression and refrigeration of the overheads stream is degassed, to produce a purified stream of liquid anhydrous hydrogen chloride and a vapor stream containing the remainder of the hydrogen and other non-condensable gases contained in the overheads stream but not recovered in the vapor stream from said compression and refrigeration steps.

8. A process as defined in claim 7, wherein the vapor stream from said degassing is combined with said vapor stream from said compression and refrigeration steps, and the combination is recycled in whole or in part to the process for reacting the chlorinated hydrocarbon feedstock and hydrogen.

9. A process as defined in claim 8, wherein any remaining portion of the combined vapor streams is contacted with water or an HCl-lean scrubbing solution to recover concentrated hydrochloric acid therefrom.

10. A process as defined in claim 2, wherein the liquid anhydrous hydrogen chloride-containing stream from the compression and refrigeration steps is cross-exchanged with the effluent from the compression step to reduce refrigeration requirements for recovering said desired proportion of said hydrogen chloride in said effluent in liquid anhydrous form.

11. A process for producing a desired less-chlorinated hydrocarbon or hydrocarbons and hydrogen chloride, with at least some of the hydrogen chloride being in anhydrous form, from a chlorinated hydrocarbon feedstock which comprises the steps of:
    reacting the chlorinated hydrocarbon feedstock and hydrogen in the presence of a suitable catalyst, under conditions effective to form a product stream comprising the desired less-chlorinated hydrocarbon or hydrocarbons and hydrogen chloride;
    distilling the product stream from such catalytic process at a pressure equal to or greater than employed in reacting the chlorinated hydrocarbon and hydrogen in said catalytic process, to produce a bottoms stream comprising about 95 percent by weight or more of the less-chlorinated hydrocarbon or hydrocarbons in the product stream and an overheads stream comprising about 95 percent by weight or greater of the hydrogen chloride in the product stream, together with unreacted hydrogen and any other non-condensable gases contained in said product stream; and
    compressing and refrigerating the overheads stream to produce a desired proportion of the hydrogen chloride in the overheads stream in a liquid anhydrous form, and a vapor stream containing substantially all of the unreacted hydrogen and other non-condensable gases if any from said overheads stream.

12. A process as defined in claim 11, further comprising distilling the bottoms stream to recover the less-chlorinated hydrocarbon or hydrocarbons in the product stream and to enable recycling of unreacted chlorinated hydrocarbon feedstock to the catalytic process.

13. A process as defined in claim 11, wherein the bottoms stream resulting from the distillation of the product stream contains about 99.5 percent by weight or more of the less-chlorinated hydrocarbon or hydrocarbons in said product stream.

14. A process as defined in claim 11, wherein the distillation of the product stream is performed at a pressure which is substantially the same as employed in the process of reacting the chlorinated hydrocarbon feedstock with hydrogen to produce said product stream.

15. A process as defined in claim 11, wherein the overheads stream from the distillation of said product stream contains about 99.99 percent by weight or greater of the hydrogen chloride in the product stream.

16. A process as defined in claim 11, wherein a portion of the liquid anhydrous hydrogen chloride-containing stream from the compression and refrigeration of the overheads stream is degassed, to produce a purified stream of liquid anhydrous hydrogen chloride and a vapor stream containing the remainder of the hydrogen and other non-condensable gases contained in the overheads stream but not recovered in the vapor stream from said compression and refrigeration steps.

17. A process as defined in claim 16, wherein the vapor stream from said degassing is combined with said vapor stream from said compression and refrigeration steps, and the combination is recycled in whole or in part to the process for reacting the chlorinated hydrocarbon feedstock and hydrogen.

18. A process as defined in claim 17, wherein any remaining portion of the combined vapor streams is contacted with water or an HCl-lean scrubbing solution to recover concentrated hydrochloric acid therefrom.

19. A process as defined in claim 11, wherein the liquid anhydrous hydrogen chloride-containing stream from the compression and refrigeration steps is cross-exchanged with the effluent from the compression step to reduce refrigeration requirements for recovering said desired proportion of hydrogen chloride in said effluent in liquid anhydrous form.

20. A process as defined in claim 11, wherein the catalytic process is conducted in the gas phase and the chlorinated hydrocarbon feedstock to such catalytic process is cross-exchanged with the product stream from such process to at least partially condense the product stream prior to distillation of the same.

21. A process as defined in claim 20, wherein a portion of the liquid anhydrous hydrogen chloride-containing stream from the compression and refrigeration of the overheads stream is degassed, to produce a purified stream of liquid anhydrous hydrogen chloride and a vapor stream containing the remainder of the hydrogen and other non-condensable gases contained in the overheads stream but not recovered in the vapor stream from said compression and refrigeration steps.

22. A process as defined in claim 21, wherein the vapor stream from said degassing is combined with said vapor stream from said compression and refrigeration steps, and the combination is recycled in whole or in part to the process for reacting the chlorinated hydrocarbon feedstock and hydrogen.

23. A process as defined in claim 22, wherein the product stream is further cross-exchanged with the combined vapor streams, prior to distillation of the product stream.

24. A process as defined in claim 11, wherein the chlorinated hydrocarbon feedstock is comprised of one or more waste or less-desired co-product chlorinated $C_3$ hydrocarbons from a chlorohydrin process of making propylene oxide or from allyl chloride/epichlorohydrin production, or is comprised of one or more waste or less-desired co-product chlorinated $C_2$ hydrocarbons from the production of vinyl chloride via ethylene dichloride.

25. A process as defined in claim 11, wherein the chlorinated hydrocarbon feedstock is reacted with hydrogen to form a product stream comprising a non-chlorinated hydrocarbon product as a desired less-chlorinated hydrocarbon as well as hydrogen chloride, and wherein the non-chlorinated hydrocarbon is separated in the bottom stream from the distillation step and is thereafter separated from any unreacted chlorinated hydrocarbon feedstock remaining in the product stream.

* * * * *